United States Patent
Luce et al.

[11] Patent Number: 5,984,476
[45] Date of Patent: Nov. 16, 1999

[54] OPHTHALMIC INSTRUMENT HAVING SELF-CALIBRATING OPTICAL SYSTEM

[75] Inventors: David A. Luce, Clarence Center; Douglas H. Hoover, Corfu, both of N.Y.

[73] Assignee: Leica Microsystems, Inc., Depew, N.Y.

[21] Appl. No.: 09/233,881

[22] Filed: Jan. 20, 1999

[51] Int. Cl.[6] .................................................. A61B 3/10
[52] U.S. Cl. ............................................................... 351/212
[58] Field of Search ..................................... 351/205, 211, 351/212, 221, 246, 247; 356/237.2, 445, 376

[56] References Cited

U.S. PATENT DOCUMENTS

| | | | |
|---|---|---|---|
| 3,883,235 | 5/1975 | Lynn et al. | 351/246 |
| 4,998,819 | 3/1991 | Labinger et al. | 351/247 |
| 5,080,477 | 1/1992 | Adachi | 351/212 |
| 5,106,183 | 4/1992 | Yoder, Jr. | 351/212 |

Primary Examiner—George Manuel
Attorney, Agent, or Firm—Simpson, Simpson & Snyder

[57] ABSTRACT

An objective refractor, having light source and detection paths intersecting at a beamnsplitter uses light normally lost during testing of an eye to self-calibrate for optical errors introduced during production of the instrument.

20 Claims, 1 Drawing Sheet

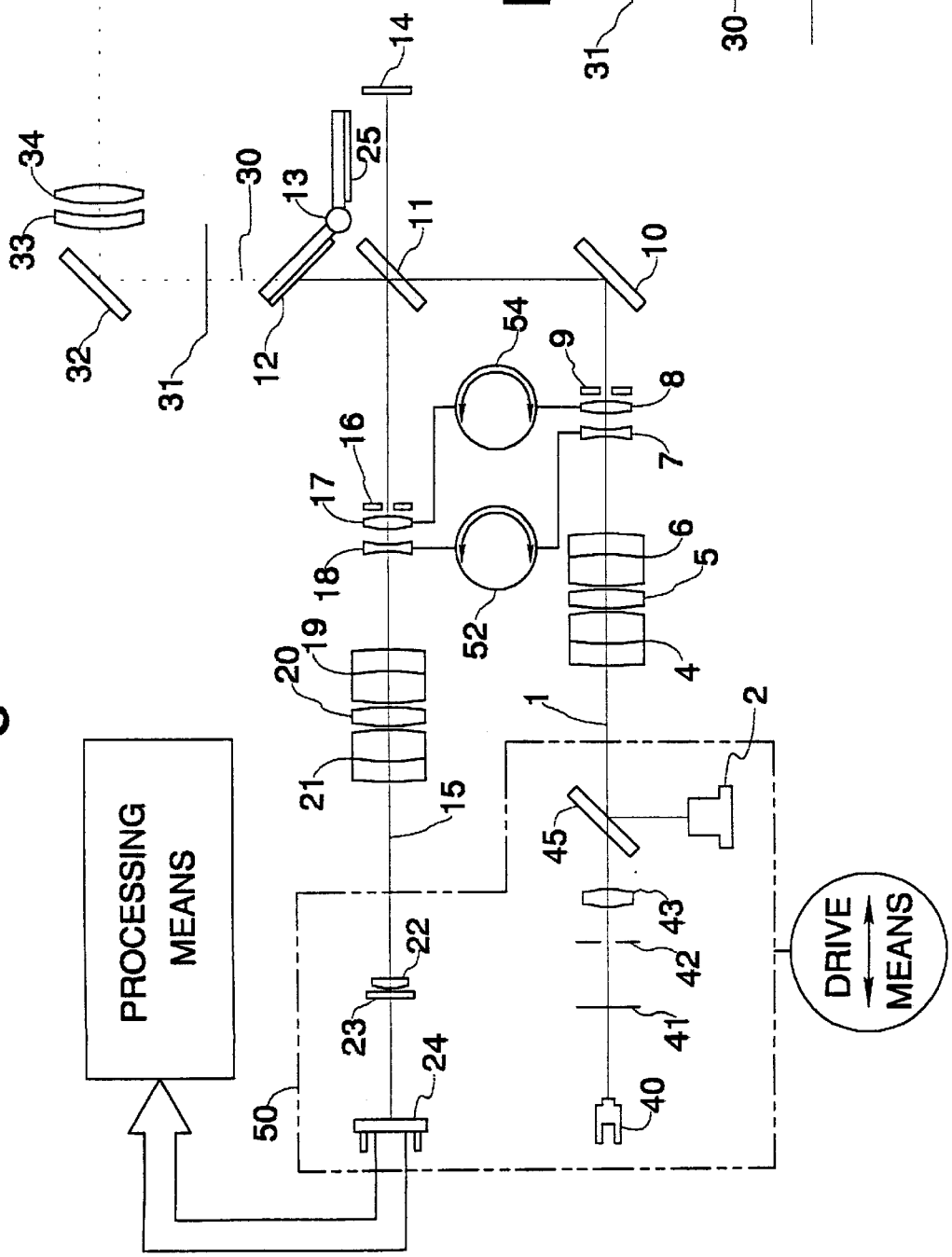
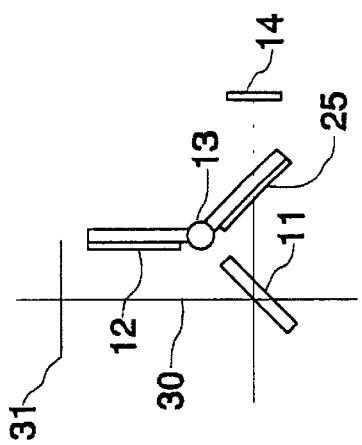

OPHTHALMIC INSTRUMENT HAVING SELF-CALIBRATING OPTICAL SYSTEM

BACKGROUND

A. Field of the Invention

This invention relates to self-calibration of ophthalmic instruments and, in particular, objective refractors.

B. Description of the Prior Art

The typical objective refractor has a light source, usually in the infrared band, that provides a beam of light that is reflected by the findus of a patient's eye to a detector. A lens system movable along the instrument axis is used to incrementally shift the image plane from one side of the fundus to the other side. The signal generated by the detector is then evaluated to determine the amount of refractive spherical error in the eye using the position of the lens system when the condition of "best focus" occurred. Rotational movement about the instrument axis is similarly used to determine the amount and axis of refractive cylindrical error. The calibration of these instruments is extremely difficult and time consuming, since the position and orientation of each optical element is critical to obtaining accurate results. In objective refractors that have one or more components on a retro-reflective path, errors introduced on the way to the eye are canceled by the same component(s) as the light reflected by the findus passes through them on the way from the eye. Even after precision alignment, the production instruments still retain some error due to inconsistencies in components and their alignment. Such errors are usually "removed" at the factory by compensation using software and/or hardware to report corrected values.

Usually objective refractors have at least one beamsplitter and several paths to be joined to and/or separated from a common path. As those skilled in the art know, beamsplitters transmit part of the light and reflect part of the light striking them and either the transmitted or reflected light is lost.

SUMMARY OF THE INVENTION

An objective refractor that is self-calibrating each time the instrument is turned on has a path selector blocking light transmitted by a beamsplitter along a testing path, while normally wasted light reflected by the beam-splitter is reflected by a dispersing surface to a detector generating a signal. The signal is evaluated by a processing means to determine the location of a carrier at the condition of best focus. The path selector is pivoted to block the normally wasted light on the calibrating path from reflecting from the dispersing surface to the detector during normal testing of an eye.

BRIEF DESCRIPTION OF THE DRAWINGS

The nature and mode of operation of the present invention will now be more fully described in the following detailed description of the preferred embodiments taken with the accompanying drawing figures, in which:

FIG. 1 is plan view of the optical arrangement of the present invention during self-calibration; and FIG. 1a is a partial plan view of the alternate position of the path selector during testing of the eye.

DESCRIPTION OF THE PREFERRED EMBODIMENT

Referring to FIG. 1, an illumination path 1 has, in sequence, a diode 2 providing a point source of light, a biconvex positive doublet 4, a biconvex positive singlet 5, a biconvex positive doublet 6, a biconcave negative cylinder lens 7, a biconvex positive cylinder lens 8, the respective cylindrical axes of lenses 7 and 8 being parallel, a field stop 9, a mirror 10, and a beamsplitter 11. Fifty percent of the light passes through beamsplitter 11 and is intercepted by an absorbent surface 12 of a path selector 13; while fifty percent of the light is reflected by beamsplitter 11 to form an image of the point source on a dispersing surface 14. The light reflected by dispersing surface 14 is divided beamsplitter 11, with fifty percent of the light passing through beamsplitter 11 on detection path 15, which has, in sequence, a field stop 16, a biconvex positive cylinder lens 17, a biconcave negative cylinder lens 18, a biconvex positive doublet 19, a biconvex positive singlet 20, a biconvex positive doublet 21, a plano-convex relay lens 22, a visible light filter 23, and an area detector 24, which generates a signal representative of reflected light from dispersing surface 14.

Referring to FIG. 1a, path selector 13 is illustrated after being pivoted to swing absorbent surface 12 off retro-reflecting test path 30 and intercept light reflected by beamsplitter 11 with absorbent surface 25. Both absorbent surface 12 and absorbent surface 25 are preferably aligned oblique to their respective paths to divert any unabsorbed light from the optical plane. In this regard, absorbent surfaces 12 and 25 may be "black mirrors" designed to absorb a very high percentage of light, with any reflected light such as from dielectric reflection being directed out of the optical system. Referring again to FIG. 1, retro-reflecting test path 30 has, in sequence, an intermediate image plane 31, a mirror 32, a convex-concave negative lens 33 and a biconvex positive lens 34 to form an image of the point source on fundus 35 of eye 36. To assist the patient, a diode 40 projects visible light through a target 41, a stop 42, and a biconvex aspheric fogging lens 43 along a path 44 intersecting illumination path 1 at beam-splitter 45.

A carrier indicated by dotted line 50 supporting point source 2 and detector 24 is selectively moved along a parallel portion of axes 1 and 15 to vary the vergence of light passing through lenses 4, 5 and 6 causing the location of intermediate image plane 31 to move similarly along axis 30. Lenses 33 and 34 act as a telescope directing parallel light at the eye, when intermediate image plane 31 is at their focal point and a normal eye will image point source 2 on fundus 35, while eyes having spherical error will image point source 2 on fundus 35 at some other location of intermediate image plane 31 along axis 30. The image of light retro-reflected from fundus 35 is treated identically by lenses 19, 20 and 21 before presentation to detector 24. An evaluation system, described in concurrently filed application Ser. No. 09/234,723, entitled "Automatic Optometer Evaluation Method Using Data Over A Wide Range Of Focusing Positions", determines the precise location of carrier 50 when the best image of point source 2 is presented to detector 24. Those skilled in the art will understand that lenses 4, 5 and 6 are selected to provide a system (Badal) having a linear relationship between the location of carrier 50 and spherical error in eye 36. Lenses 19, 20 and 21 are as identical to lenses 4, 5 and 6 as permitted by manufacturing. During calibration, carrier 50 is moved to determine the precise location when the "best focus" image of point source 2 is presented to detector 24 from dispersing surface 14. This location can be used as a reference location for subsequently conducted tests because all optical elements affecting the test results are included in determining the reference location, except those optical elements introducing errors self-corrected by retro-reflection. Similarly, a rotational reference location is determined for equal and opposite cylinder lenses 7 and 8 as well as equal and opposite cylinder lenses 17 and 18, when the "best focus" image of point source 2 is presented to detector 24 from dispersing surface 14. Lenses 7 and 18 are connected to be rotated simultaneously by motor 52 and lenses 8 and 17 likewise rotated simultaneously by motor 54. Since lenses 7 and 8, as well as lenses 17 and 18, are equal and opposite, they should introduce no cylinder to the instrument when their cylinder axes are aligned. The linear (spherical) and rotational (cylindrical) reference positions are compared at the factory to a test eye (ISO) to determine any value of sphere and/or cylinder at the reference positions. These values are stored in the processing means and deducted from values obtained during tests conducted on an eye.

What is claimed is:

1. An ophthalmic instrument for testing an eye comprising: an illumination path, a point light source positioned at the beginning of said illumination path, a first plurality of optical elements spaced along said illumination path, a beamsplitter positioned at the end of said illumination path, a retro-reflecting path beginning and ending at said beamsplitter, an intermediate image plane located on said retro-reflecting path, a detection path beginning at said beamsplitter, a second plurality of optical elements spaced along said detection path, detector means for generating a signal representing an image of said light source positioned at the end of said detection path, drive means to selectively change positions of said point light source and said detector means as a unit along their respective paths, a surface reflecting light from said point source to said detection path that is reflected by said beamsplitter, and means to determine the position of said unit at best focus of said image, whereby errors introduced by said first and second plurality of optical elements are calibrated.

2. The ophthalmic instrument of claim 1, wherein said detector means is an area detector and is confocal, with respect to both said intermediate image plane and said surface, to said light source.

3. The ophthalmic instrument of claim 2, wherein each of said first and second plurality contain elements for changing the vergence of light when the positions of said light source and detector are changed by said drive means.

4. The ophthalmic instrument of claim 3, wherein each of said plurality contain a pair of equal and opposite cylinder lenses, a first motor to rotate one cylinder lens of each pair and a second motor to rotate the other lens of each pair.

5. The ophthalmic instrument of claim 4, wherein said light source emits infrared light.

6. The ophthalmic instrument of claim 5, further including target means for projecting visible light along said illumination path and filter means for blocking visible light from said detector.

7. The ophthalmic instrument of claim 1, further including a path selector, a pair of light absorbing surfaces connected to said selector, one of said pair of surfaces selectively intercepting light from said light source passing through said beamsplitter and the other of said pair of surfaces alternatively intercepting light from said light source reflected by said beamsplitter.

8. The ophthalmic instrument of claim 7, wherein each of said pair of surfaces is a black mirror.

9. The ophthalmic instrument of claim 8, wherein each of said pair of surfaces is angled to alternatively deflect unabsorbed light from the beamsplitter.

10. The ophthalmic instrument of claim 9, wherein said path selector is pivotal.

11. The ophthalmic instrument of claim 10, wherein said detector means is an area detector and is confocal, with respect to both said intermediate image plane and said surface, to said light source.

12. The ophthalmic instrument of claim 11, wherein each of said first and second plurality contain elements for changing the vergence of light when the positions of said light source and detector are changed by said drive means.

13. The ophthalmic instrument of claim 12, wherein each of said plurality contain a pair of equal and opposite cylinder lenses, first motor to rotate one cylinder lens of each pair and second motor to rotate the other lens of each pair.

14. The ophthalmic instrument of claim 13, wherein said light source emits infrared light.

15. The ophthalmic instrument of claim 14, further including target means for projecting visible light along said illumination path and filter means for blocking visible light from said detector.

16. In an objective refractor having a light source and optical elements along an illumination path, a detector and optical elements along a detection path and optical elements along a retro-reflection path, said paths intersecting at a beamsplitter, the invention comprising a calibration path intersecting said illumination, detection and retro-reflection paths at said beamsplitter, said beamsplitter directing normally wasted light along said calibration path to a dispersing surface and a path selecting means for alternatively blocking said retro-reflecting path or said calibration path, whereby said refractor is calibrated using light otherwise wasted in said refractor.

17. In an objective refractor according to claim 16, wherein said path selecting means has two absorbent surfaces.

18. In an objective refractor according to claim 17, wherein the optical elements along said illumination path produce an intermediate image of the illumination source on said retro-reflection path.

19. In an objective refractor according to claim 18, wherein each of said two surfaces is a black mirror positioned on said selecting means to direct unabsorbed light off the respective blocked path.

20. In an objective refractor according to claim 16, wherein the optical elements along said illumination path produce an intermediate image of the illumination source on said retro-reflection path.

\* \* \* \* \*